United States Patent [19]

Tseng et al.

[11] Patent Number: 5,274,120

[45] Date of Patent: Dec. 28, 1993

[54] 1-VINYL-3(E)-ETHYLIDENE PYRROLIDONE

[75] Inventors: Susan Y. Tseng, Staten Island, N.Y.; Philip F. Wolf, Bridgewater, N.J.

[73] Assignee: ISP Investments Inc., Wilmington, Del.

[21] Appl. No.: 25,523

[22] Filed: Mar. 3, 1993

[51] Int. Cl.$^5$ .................................... C07D 207/263
[52] U.S. Cl. .................................................. 548/543
[58] Field of Search ........................................ 548/543

[56] References Cited

PUBLICATIONS

Haaf et al, Polymer Journal, vol. 17, No. 1, pp. 143–152 (1985).

*Primary Examiner*—David B. Springer
*Attorney, Agent, or Firm*—Walter Katz; Marilyn J. Maue; Joshua J. Ward

[57] ABSTRACT

What is provided herein is 1-vinyl-3(E)-ethylidene pyrrolidone in a purity of at least 95%, in the form of white, needle-shaped crystals having a melting point of 59°–61° C.

1 Claim, No Drawings

1-VINYL-3(E)-ETHYLIDENE PYRROLIDONE

BACKGROUND OF THE INVENTION

1. Field of the Invention

This invention relates to vinylpyrrolidones, and, more particularly, to 1-vinyl-3(E)-ethylidene pyrrolidone (EVP), and to a method for obtaining this isomeric compound.

2. Description of the Prior Art

Crosslinked polyvinylpyrrolidone is made by popcorn or proliferous polymerization of vinylpyrrolidone, in the absence or presence of crosslinking agents, as described in U.S. Pat. Nos. 3,277,066; 3,306,886; 3,759,880; 3,933,766; and 3,992,562; and in an article by F. Haaf et al. in Polymer J. 17 (1), p. 143-152 (1985), entitled, "Polymers of N-Vinylpyrrolidone: Synthesis, Characterization and Uses." Polymerization of vinylpyrrolidone can occur in the absence of added crosslinker because the requisite crosslinker in the process is formed in situ during the first stage heating of vinylpyrrolidone in aqueous caustic solutions at temperatures >100° C., e.g. at 140° C. Such bifunctional monomers, identified as 1-vinyl-3-ethylidene pyrrolidone and ethylidene-bis-3-(N-vinylpyrrolidone), are observed by gas chromatography and other analytical techniques to be present in small amounts in reaction mixtures which had been cooled to room temperature. However, after the polymerization was completed, these bifunctional compounds, could not be found in the final product. Accordingly, the named bifunctional monomers are present only in small amounts as intermediates during the polymerization and are consumed in the process of forming the crosslinked PVP polymer.

Accordingly, an object of this invention is to provide the isomeric compound 1-vinyl-3(E)-ethylidenepyrrolidone in a purity of at least 95%.

These and other objects and features of the invention will be made apparent from the following description of the invention.

SUMMARY OF THE INVENTION

What is provided herein is the isomeric compound 1-vinyl-3(E)-ethylidene pyrrolidone (EVP) having the formula:

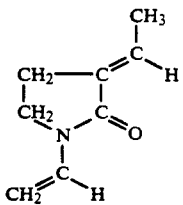

in a purity of at least 95%, in the form of white, needle-shaped crystals having a melting point of 59°-61° C.

This isomeric compound exists in the (E) form, which is defined as the isomer in which the methyl group of the ethylidene radical is positioned away from the oxygen atom of the pyrrolidone ring.

The desired isomeric compound is obtained herein in high yield by reaction of vinylpyrrolidone in aqueous strongly basic solution, in a 2-phase aqueousorganic system, at an elevated temperature, under vigorous agitation. The isomeric compound is recovered from the reaction product by extraction with an organic solvent and fractional distillation, or by direct fractional distillation of the organic fraction of the reaction product.

DETAILED DESCRIPTION OF THE INVENTION

In accordance with the present invention, the desired isomeric EVP compound is produced in a 2-phase reaction mixture comprising an organic phase of vinylpyrrolidone monomer present in an amount of about 25-90%, preferably 40-75%, and, most preferably, about 50%, by weight of the reaction mixture, and an aqueous phase which is a strongly aqueous basic solution, such as caustic (NaOH or KOH), or a tetraalkyl ammonium hydroxide solution, suitably with a base concentration of about 2-50%, preferably about 5-10%, by weight of the mixture. The reaction mixture is heated to a reaction temperature of about 120°-170° C., preferably 130°-140° C., in a closed system, under an inert atmosphere, at ordinary or higher initial pressures, suitably at an initial pressure of 0-3 bars of an inert gas, such as nitrogen. The reaction to convert VP monomer to isomeric EVP compound is carried out for about 0.5-10 hours, preferably 1-3 hours, at, e.g. 140° C., while the reaction mixture is subjected to vigorous agitation, e.g. about 800 rpm.

At the conclusion of the reaction, 2 layers are obtained as the reaction product. The top layer is an organic layer which contains about 50-80% by weight of unreacted VP and about 5-30% of the desired isomeric EVP compound, and, more particularly, about 70-75% VP and 15-20% EVP. The bottom layer is an aqueous caustic layer which also contains some some unreacted VP and a small amount of EVP.

The isomeric compound then is isolated from the reaction product by extraction with an organic solvent and fractional distillation, or by direct fractional distillation of the organic (top) layer.

In the extraction technique, the reaction product is treated with a volatile organic solvent, such as chloroform, heptane, or petroleum ether, and the extract is washed successively with a saturated salt solution, then distilled water, and the volatile organic solvent is removed by distillation under reduced pressure. The residue is distilled at 60°-90° C. (1-2 mm Hg) to remove unreacted vinylpyrrolidone monomer and by-products of the reaction, including 2-pyrrolidone. Then, at 80°-90° C., a second fraction is collected as a solid. Upon recrystallization of the solid product from water and drying, the desired isomeric (E) compound is obtained as white, needle-shaped crystals having a melting point of 59°-61° C. The (E) isomer structure is confirmed by gas chromatographic, mass spectroscopy and $^1H_2$ and $^{13}C$ NMR analysis.

In the direct distillation method of recovery of the isomeric compound from the reaction mixture, the organic phase, which is the top layer, is separated from the aqueous caustic solution, which is the bottom layer, and then the organic layer is flash distilled under vacuum. A suitable vacuum distillation apparatus includes a receiving condenser connected to the distilling head at one end and to a receiving flask at the other end. The unreacted VP and 2-pyrrolidone by-products are distilled out from the organic layer as a clear liquid at 75°-90° C. at 2 mm Hg. The isomeric compound then is flash distilled as a colorless solid which crystallizes on the walls of the receiving condenser. This solid can be collected from the walls, or, preferably, the walls are heated to melt the solid to a liquid, and the liquid is recovered and solidified. Upon recrystallization from water, or from a water-acetone mixture, the desired isomeric compound is obtained as pure solid.

The process of rapid and efficient production of EVP in large quantities herein is based on the following two interdependent parameters.

(1) An initial high concentration of caustic catalyst in the reaction mixture, and (2) Maintenance of a two-phase organic/aqueous system in the reaction mixture throughout the course of the reaction.

The use of a high (2-50%) caustic concentration has a dual effect. First the inorganic hydroxide causes the aqueous layer to maintain its integrity and "salt out" the organic compounds, most notably, vinylpyrrolidone (VP). Such is not the case for conventional PVP syntheses using a low concentration caustic solution in which the aqueous and organic phases merge. Secondly, the high caustic concentration in this process accelerates the reaction. Indeed, the caustic, which is a catalyst for the formation of EVP from VP, is consumed through reaction with 2-pyrrolidone, a byproduct of the reaction. The 2-pyrrolidone, in turn, is readily hydrolyzed by base to sodium 4-aminobutyrate (4-AB), which is not a catalyst for EVP formation. However, (4-AB), being water soluble, can serve as the salt necessary to maintain the 2-phase system in the process.

During the process, transfer of the vinyl moiety which is necessary for EVP synthesis appears to take place at or near the organic-water interface. Once the VP transfer is complete, the slightly acidic 2-pyrrolidone by-product drifts into the basic aqueous phase and EVP moves to the organic medium. In fact, both the strong base and other salts are present overwhelmingly in the aqueous layer during the process. The conversion of 2-pyrrolidone to 4-AB in the presence of aqueous base reduces the concentration of base in the organic phase, thereby avoiding an undesired further reaction of EVP to ethylidene-bis-vinylpyrrolidone (EVBP).

The yield of isomeric EVP obtained in the process of the invention is about 5-30% based on reacted VP.

The invention will now be illustrated with reference to the following examples.

EXAMPLE 1

A 1-1 reaction vessel equipped with a reflux condenser and a mechanical stirrer was charged with 100 g of vinylpyrrolidone (VP monomer and 300 g of B.F. Goodrich Caustic 20 solution (20% NaOH). The 2-phase reaction mixture was given a blanket of nitrogen and heated to 100° C. where it was held for 5 hours while stirring vigorously at 800 rpm. Then the reaction product was extracted with chloroform and the organic layer (the bottom layer) was collected and washed several times with a saturated NaCl solution until the final aqueous washing was neutral. The chloroform was removed by rotary evaporation at room temperature. Thereafter, the organic product was fractionally distilled at 60°-90° at 1 mm Hg to remove 20 g of unreacted vinylpyrrolidone monomer, and the 2-pyrrolidone by-product. Then at 80°-90° C. a solid product was collected which was recrystallized from ice water and dried in a desiccator. A total of 9.3 g of white, needle-shaped crystals were obtained having a sharp melting point of 59°-61° C. The isomeric compound was identified as 1-vinyl-3(E)-ethylidene pyrrolidone having a purity of >95% by GC/MS[1]H and $^{13}$C NMR analysis. The yield was 11.6% based upon the amount of VP reacted.

$$\% \ EVP \ \text{Yield} = \frac{9.3 \ [EVP]}{[100(\text{Initial } VP) - 20(\text{Unreacted } VP)]} \times 100$$

EXAMPLE 2

The procedure of Example 1 was followed using a reaction mixture of 150 g of VP, 180 g of a 50 wt. % NaOH solution and 270 g of distilled water. A total of 8.7 g of the isomeric compound was obtained. The yield was 7.3%.

EXAMPLES 3-5

The procedure of Example 2 was followed using reaction periods of 7, 14 and 21 hours. The respective yields were 9.7%, 18.5%, 28%.

EXAMPLES 6-7

A stainless steel Buchi reactor was used as the reaction vessel at an initial pressure of 3 bars of nitrogen pressure and at room temperature. The reaction was carried out at 140° C. for 2 hours using 320 g of VP, 40 g of 50% NaOH solution and 40 g of distilled water (Ex. 6), and 320 g of VP and 80 g of 50% NaOH solution (Ex. 7), to provide yields of 25%, and 28%, respectively, of the isomeric compound.

EXAMPLE 8

A reaction mixture of 80% VP and 5% NaOH was heated at 140° C. for 2 hours under 3 bars of $N_2$ pressure (14 ppm $O_2$ only). The organic reaction product (top layer) was separated from the aqueous phase; it was found to contain 75% VP and about 19% of the isomeric (E) compound based on the total mixture of the top layer.

The top layer was then flash distilled at 75°-95° C. under 1 mm Hg and VP and 2-pyrrolidone was collected in the receiving flask. The isomeric compound vapor was distilled at 80°-90° C. and solidified on the condenser. The condenser then was heated to 70° C. and isomeric compound was collected as a liquid in the receiving flask. Upon cooling to a solid, the isomeric compound was recrystallized in the cold from a mixture of acetone/water. The yield of isomeric EVP was 26%.

The isomeric EVP compound of the invention finds utility as a crosslinking agent in the direct polymerization of vinylpyrrolidone to crosslinked polyvinylpyrrolidone at low temperatures.

While the invention has been described with particular reference to certain embodiments thereof, it will be understood that changes and modifications may be made which are within the skill of the art. Accordingly, it is intended to be bound only by the following claims, in which:

What is claimed is:

1. The compound 1-vinyl-3(E)-ethylidene pyrrolidone having the formula:

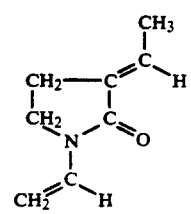

in the form of white, needle-shaped crystals having a melting point of 59°-61° C.

* * * * *